US008568231B2

(12) United States Patent
Solanki et al.

(10) Patent No.: US 8,568,231 B2
(45) Date of Patent: Oct. 29, 2013

(54) VIRTUAL REALITY ENTERTAINMENT SYSTEM FOR TREATMENT OF PHANTOM LIMB PAIN AND METHODS FOR MAKING AND USING SAME

(75) Inventors: Daneshvari R. Solanki, League City, TX (US); Thomas K. Doan, Austin, TX (US); William E. McGrady, II, Texas City, TX (US)

(73) Assignee: The Board of Regents of the University of Texas System, Austin, TX (US)

( * ) Notice: Subject to any disclaimer, the term of this patent is extended or adjusted under 35 U.S.C. 154(b) by 217 days.

(21) Appl. No.: 12/870,563

(22) Filed: Aug. 27, 2010

(65) Prior Publication Data

US 2011/0065505 A1 Mar. 17, 2011

Related U.S. Application Data

(60) Provisional application No. 61/237,481, filed on Aug. 27, 2009.

(51) Int. Cl.
*A63F 13/00* (2006.01)
*A61N 1/00* (2006.01)
*A61F 2/48* (2006.01)

(52) U.S. Cl.
USPC .................. 463/36; 463/30; 607/54; 623/24

(58) Field of Classification Search
USPC .................. 463/36; 623/24; 607/54
See application file for complete search history.

(56) References Cited

U.S. PATENT DOCUMENTS 7,717,962 B2 * 5/2010 Wilson ........................... 623/24
2008/0306572 A1 * 12/2008 Osada et al. .................... 607/54
2011/0009194 A1 * 1/2011 Gabai et al. .................... 463/36

OTHER PUBLICATIONS

Chan, BL et al "Mirror Therapy for Phantom Limb Pain" New England Journal of Medicine (2007) 357:21, pp. 2206-2207.
MacLachlan, M et al "Mirror Treatment of Lower Limb Phantom Pain; A case Study" Disability and Rehabilitation (2004) 26:14/15, pp. 901-904.
McCabe, CS et al "A controlled pilot study of the utility of mirror visual feedback in the treatment of complex regional pain syndrome (type 1)" Rheumatology (2003) 42: pp. 97-101.
Murray CD, et al "Investigating the efficacy of a virtual mirror box in treating phantom limb pain in a sample of chronic sufferers" Int J Disabil Human Dev (2006) 5(3): pp. 227-234.
Murray CD, et al "The treatment of phantom limb pain using immersive virtual reality: Three case studies" Dirability and Rehabilitation (2007) pp. 1-5, i-First article.

* cited by examiner

*Primary Examiner* — Arthur O. Hall
*Assistant Examiner* — Jeffrey Wong
(74) *Attorney, Agent, or Firm* — Wong, Cabello, Lutsch, Rutherford & Brucculeri, LLP.

(57) ABSTRACT

Visual feedback systems and methods implementing the system are disclosed that use computer generated images of lost limbs to display visual images of the limb being used in activities on a display unit providing visual feedback of the use of the missing limb to the brain to ameliorate, reduce, treat or eliminate phantom limb pain.

12 Claims, 5 Drawing Sheets

*VIRTUAL REALITY ENTERTAINMENT SYSTEM FOR TREATMENT OF PHANTOM LIMB PAIN AND METHODS FOR MAKING AND USING SAME*

RELATED APPLICATIONS

This application claims the benefit of and priority to U.S. Provisional Application Ser. No. 61/237,481, filed 27 Aug. 2009 (Aug. 27, 2009).

BACKGROUND OF THE INVENTION

1. Field of the Invention

Embodiments of the present invention relate to virtual reality systems that use a phantom limb and not the normal limb to provide visual feedback to the brain to ameliorate, reduce, treat or eliminate phantom limb pain (PLP). The systems include a gaming console so that it can be accessible, affordable and interactive.

2. Description of the Related Art

Phantom limb pain (PLP) is a genuine phenomenon in patients who have undergone an amputation. PLP is most common after an amputation of the limb. This pain can occur soon after the amputation or may develop later. The intensity of the pain varies from mild to intractable, which can disrupt the patient's life. PLP can then interfere with daily activity of living, sleeping, appetite and concentration. Incidents of patients suffering PLP varies from 30% to 80%. PLP occurs in 50-70% of amputees in the first year after limb amputation. If the patient had severe pain prior to amputation, then the patient will generally have severe pain after the amputation too. Such patients are also more likely to develop the phantom pain.

There is no single treatment that can alleviate this pain. Various modalities have been tried. So far, the only therapies that have shown promise are the "mirror box" therapy developed by Dr. Ramchandran and "virtual reality" therapy developed by Dr. Pettifer. Both of these techniques use the normal limb to perform tasks and fool or trick the brain by creating the presence of the phantom limb. This provides visual feedback to the brain, which is the most important aspect that helps in treating and managing phantom limb pain.

Thus, only therapies that provide visual feedback of the missing limb appear effective in dealing with PLP. Even though such methods as set forth above are effective, there is still a need in the art for visual feedback systems to help the patients with phantom limb pain, especially visual feedback systems that are accessible, affordable and interactive.

SUMMARY OF THE INVENTION

Embodiments of this invention provide visual feedback systems including an optional virtual feedback digital processing unit, a game console in communication with the virtual feedback digital processing unit, a game console controller in communication with the game console or the virtual feedback digital processing unit, a display unit in communication with the game console or the virtual feedback digital processing unit, a receiving signal sensor in communication with the game console or the virtual feedback digital processing unit, a first transmitting sensor associated with a normal limb, and a second transmitting sensor associated with a missing limb. In all embodiments, the connections may be wired or wireless depending on console configuration and personal preferences. The transmitting sensors transmit signals relating to motion of the normal and missing limbs that are received by the receiving sensor to produce an output signal. The game console and/or the virtual feedback digital processing unit, then, uses the output signal from the receiving sensor and a generated image of the missing limb or both limbs are displayed on the display unit to provide visual feedback to the patient. Additional transmitting sensors can be associated with other parts of the patient's body so that larger parts of the body or the whole body may be displayed as well. Thus, the patient gets a visual feedback of using the missing limb, which stimulates the brain areas previously associated with the missing limb, and which ameliorates, reduces, treats or eliminates phantom limb pain (PLP).

Embodiments of this invention provide visual feedback methods including generating an image of a patient's missing limb using computer software programs or using a mirror image of the patient's normal limb. The methods also include storing the generated image in the visual feedback digital processing unit of a system of this invention. The methods also include using the generated images to display the patient including the missing limb on the display unit. The methods also include manipulating the images to provide visual feedback to the patient associated with simulated use of the missing limb and ameliorating, reducing, treating or eliminating phantom limb pain (PLP). The methods also include using motion sensor information associated with motion of the normal limb and a portion of the body adjacent the missing limb, where motion of the normal limb and the portion of the body adjacent the missing limb are input to a game console to simulate motion of the missing limb or the normal and missing limbs for use in motion-activated games such as sports games, exercise games, or other games, thus ameliorating, reducing, treating or eliminating phantom limb pain (PLP).

BRIEF DESCRIPTION OF THE DRAWINGS

The invention can be better understood with reference to the following detailed description together with the appended illustrative drawings in which like elements are numbered the same.

DETAILED DESCRIPTION OF THE INVENTION

Figure 1:
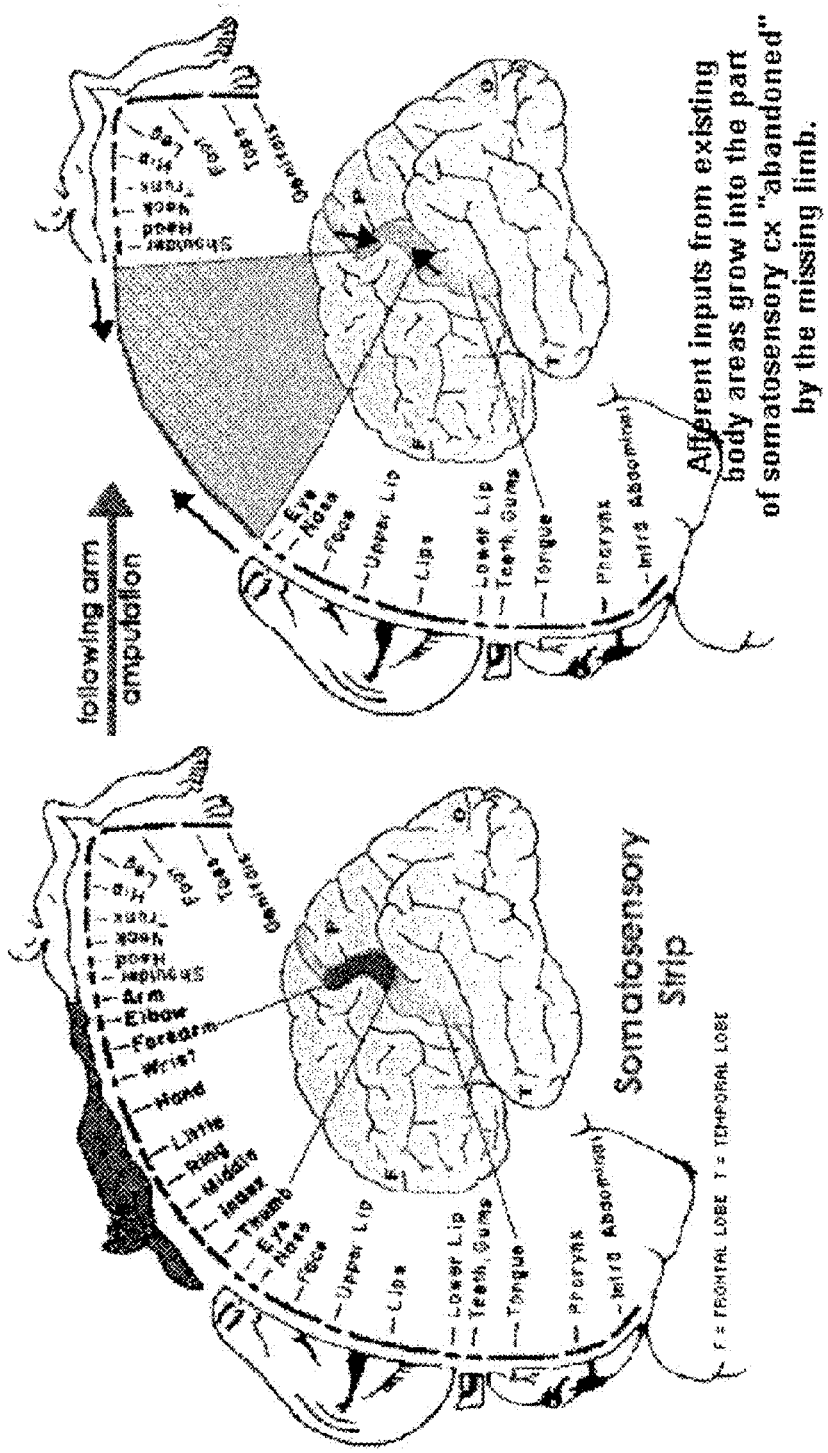
FIG. 1 depicts a somatosensory homunculus representation of the brain before and after limb amputation.

The inventors have found that a visual feedback system can be constructed for reducing phantom limb pain (PLP), where an image of a missing limb is generated and used to visually display the missing limb in activities to provide a visual feedback to a patient. The visual feedback results in a decrease of PLP in a patient that has lost a limb through injury and/or amputation. Certain embodiments of this invention use a game console as the platform for simulating visual activities using the missing limb making the system readily accessible, affordable and interactive. Such systems are ideally suited for treating phantom limb pain in patients with elective amputation due to ischemia, diabetes mellitus, infection, tumors or cancer. Such systems are also ideally suited for treating phantom limb pain in patients with traumatic amputation. Such systems are also ideally suited for treating phantom limb pain in members of the armed forces where the limbs were blown off in the war. Such systems are also ideally suited for treating phantom limb pain in with stroke who are undergoing rehabilitation.

The present methodology is different from the prior art in that we use a generated image of the phantom limb itself and a sensor associated with a portion of the body adjacent the missing limb to visually simulate activities involving the missing limb such a boxing, wrestling, fighting, bowling, playing tennis, playing football, playing soccer, swimming, playing chess, playing any other game or performing any other activity. Thus, our system provides visual feedback relating to use of the missing limb itself and not to use of the normal limb. It utilizes portable, simple, therapeutic entertainment instead of regimented tasks. It will be affordable unlike virtual reality systems that costs a million dollars. It will be easily accessible for patients in their home. It will be interactive, entertaining and fun. It will be useful for all ages.

While some embodiments of the present invention may utilize a separate system to produce or generate an image of a patient's missing limb, other embodiments may use games specifically designed to generate the missing limbs at set up time removing the need for a separate processing unit.

We believe that it could become a standard of care for the treatment of phantom limb pain because of its portability, affordability and patient compliance.

Purpose of the Invention

Phantom limb pain is a genuine phenomenon in patients who have amputations. It is most common after an amputation of the limb. This pain can occur soon after the amputation or may develop later. The intensity of the pain varies from mild to intractable that could disrupt the patient's life. It can then interfere with daily activity of living, sleep, appetite and concentration. Incidence of such phantom pain varies from 30%-80%. It occurs in 50-70% in the first year. If the patient had severe pain prior to the amputation, then they have such pain after the amputation too. They are also more likely to develop the phantom pain.

Mechanism of Phantom Pain

The exact cause of this persistent pain is not known. But various different mechanisms are described: (1) Peripheral mechanism: It may be as a result of continuous ectopic discharge from the severed nerves; (2) Central mechanism: It may be due to the reorganization in the cerebral cortex and the thalamus; (3) Psychogenic mechanism: PLP may be psychogenic in origin; and (4) Spinal mechanism: It could be secondary to the deafferentation mechanism in the spinal cord.

Treatment of Phantom Limb Pain

As there is no identifiable single cause there is no single treatment for it. Various modalities have been tried. These treatments are based on case reports. There are no randomized trials or meta-analysis for the pain physician to help guide the therapy for this pain. There is also no consensus about the most effective therapy. The modalities that have been tried are: (1) Preemptive analgesia; (2) Medications, (3) Physical means, (4) Interventional pain procedures, and (5) Complementary therapy.

Preemptive Analgesia

There is some evidence in the literature that preemptive analgesia prior to the amputation and adequate analgesia postoperatively may prevent central sensitization and cortical reorganization thereby either delaying or preventing the development of phantom limb pain. So, regional anesthesia may play a role in management of these patients.

Medications

Various classes of drugs like NSAIDs, opiates, anticonvulsants and antidepressants have been sued in the management of phantom limb pain. NSAIDs have a limited role and may be useful early on. Opiates are widely used, especially methadone because of its NMDA antagonistic activity and analgesic effect on the neuropathic pain. However often times the patients are not prescribed adequate amounts of opiates for fear of development of addiction or being affected by the regulatory agencies. Anticonvulsants are used because of their membrane stabilizing effects so they help with the shooting pain. Antidepressants help with the pain as well as the depression. A cocktail of drugs can also be used to control this pain. They may need these medications for prolonged periods so the side effects from the medications could be another problem.

Physical Means

These have been tried, but with limited success. Transcutaneous Electrical Nerve Stimulation (TENS) activates the large fibers in the substantia gelatinosa in the spinal cord and thereby close the gate. So, the responses from the small fibers do not have access to the spinal cord. This diminishes the traffic of the impulses to the spinothalamic tract leading to pain relief.

Electroconvulsive therapy (ECT) has been tried in the cases of intractable phantom limb pain with some success. The hypothesis is that it works by induction of thalamocortical changes. It might be an effective therapy but there is no conclusive evidence to prove that. The major side effect is development of retrograde and anterograde amnesia.

A myoelectric prosthesis has been tried but it too has not proven to be beneficial in reducing or controlling the phantom limb pain.

Interventional Pain Procedures

Procedures like peripheral nerve blocks, sympathetic nerve blocks, and epidural steroid injections have been tried for the phantom limb pain, stump pain and pain from the neuroma. Neurodestructive procedures have also been tried to get control of the pain. Doral Root Entry Zone (DREZ) lesions have been done to ablate the afferent input in the spinal cord. Even a spinal cord stimulator and deep brain stimulation have been tried. All these measures provide either no relief or temporary pain relief from the phantom limb pain.

Complementary Therapies

These include acupuncture, biofeedback, massage and vibration therapies. Visual imagery has been helpful. Dr. Ramchandran a neurologist interested in neuroplasticity first suggested that phantom limb pain may be due to changes in the brain rather than the peripheral nerves. In the somatosensory homunculus, the body is represented in an orderly manner. Input from the face is located next to the input from the hand Ramchandran put forth the theory that when the arm is amputated that cortical area is vacated because of the lack of the peripheral input. This territory is then invaded by the surrounding neurons of the face as shown in FIG. 1. He proved this by stroking different parts of the face that activated the original hand area of the cortex and patient felt the sensation in the phantom hand. He also showed this by using magnetoencephalography (MEG). So, Ramachandran created the "mirror box" in which a mirror is placed vertically in front of the patient. The patient looks at the mirror reflection of the normal arm so that the reflection was optically superimposed on the left location of the phantom. This created the visual illusion that the phantom had been restored.

Figure 2:
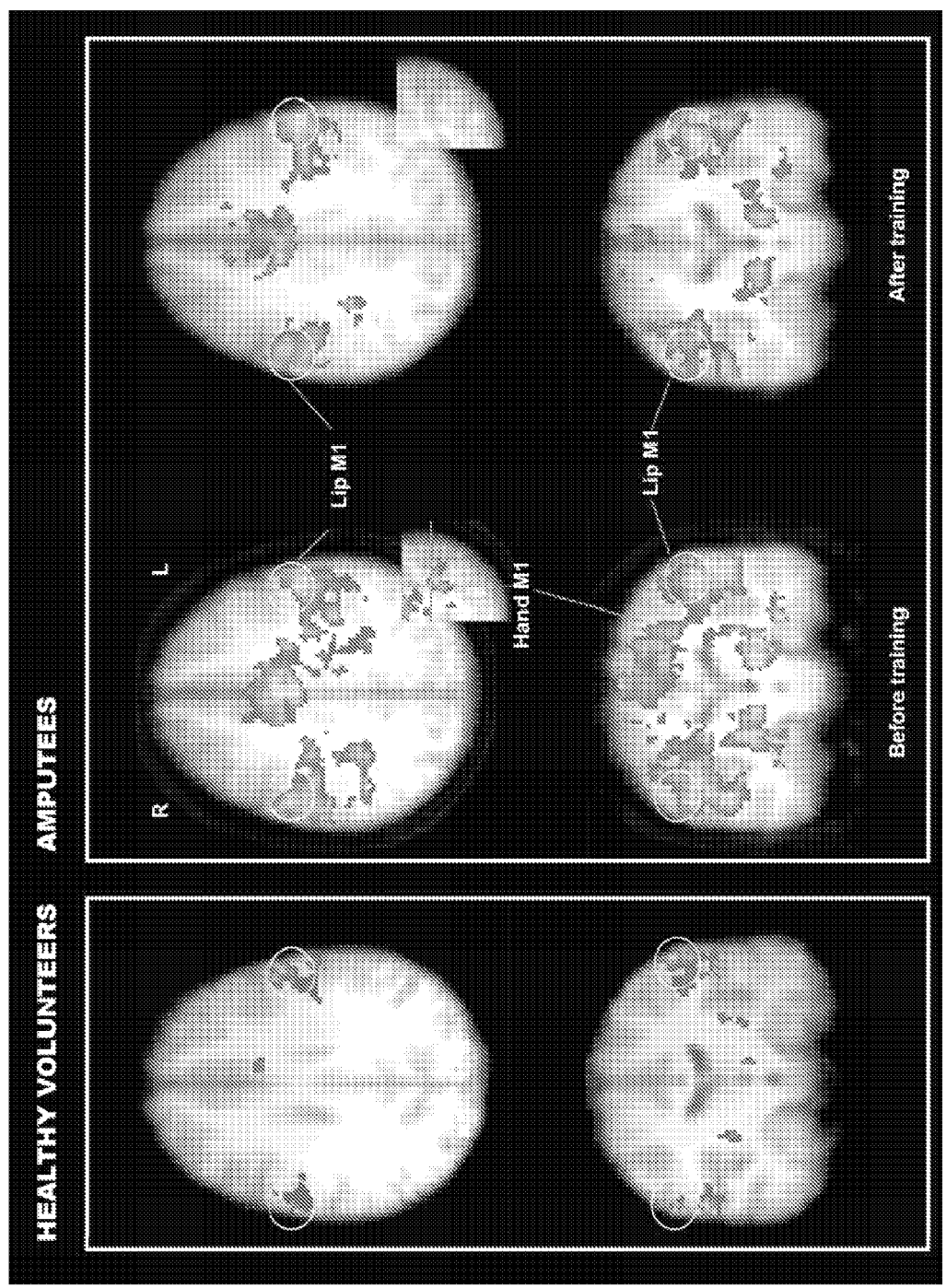
FIG. 2 depicts fMRI images showing a healthy persons brain response during lip pursing and an amputee response before and after visual feedback using a mirror box device.

The visual mirror feedback theory has now been proven by double blind placebo controlled trials in alleviation of the phantom limb pain. fMRI has also shown that when there is visual feedback from the limb, the area invaded by surrounding neurons regresses and the pain gets better when the mirror box is used as shown in FIG. 2. In 2007, Dr. Jack Tsao stated that the mirror therapy is highly effective for treating phantom limb pain in the veterans undergoing rehabilitation. In the same year, National Geographic published an article that Dr. Pettifer has utilized the concept of virtual reality system to treat phantom limb pain. Here the patient wears a head mounted display with two tiny video screens one for each eye. This creates a sensation of 3-D vision. The patient then slips on a glove on the normal hand and completes a series of tasks. It is the good arm that is doing the tasks, but in the virtual environment, they really see the missing arm performing the task. Once again this provides the visual feedback of the missing arm. The results with this vary, but has been shown to provide two days of pain relief.

Referring now to FIG. 2 in detail, the red areas in these three fMRI images indicate the parts of the cerebral cortex that were activated when healthy volunteers and amputees were asked to purse their lips. The left-hand images show that the healthy volunteers' brains carried out this action very efficiently (left): in each hemisphere, only the area representing the lips (circled in yellow) is activated, plus a small secondary motor area. The middle images show the amputees' brains carried out the same action much less efficiently, activating larger and more diffuse areas—including the hand area (inset). The right-hand images show that after performing their training exercises for a few weeks, the amputees' brains carried out this activation more efficiently—with no activation of the hand area.

Embodiments of this invention include use a game console such as an Nintendo Wii console, Sony PS console, XBOX console or similar game consoles. The consoles are used to display simulated activities involving the missing limb or limbs, decreasing PLP. Movements displayed by the console are sensed using a receiving sensor from transmitting sensors associated with a patients' healthy limb or limbs and the patient's missing limb or limbs.

In certain embodiments, we first produce a mirror image of the patients' healthy limb to produce a usable image of a patient's missing limb. One way of producing the mirror image is to place the normal limb of the amputee in a mirror box producing an image of the phantom arm. The mirror image will be stored in the visual feedback computer unit as an image of the missing limb. When this image is projected on the display unit, the patient will see his/her own missing limb or the phantom limb. This will then provide the visual feedback to the brain, which is the essential component of the treatment of phantom limb pain. The computer unit can include exercises or tasks for the patient to undergo with the normal limb resulting in simulated motion of the missing limb. Of course, the unit may also display motion by both limbs using motion transmitting sensors on both the normal and missing limbs. In other embodiments, the unit is in electronic communication with a game console so that the sensor input data is used by the game console to display visual simulations using the missing limb or both the normal and missing limb.

Figure 3:
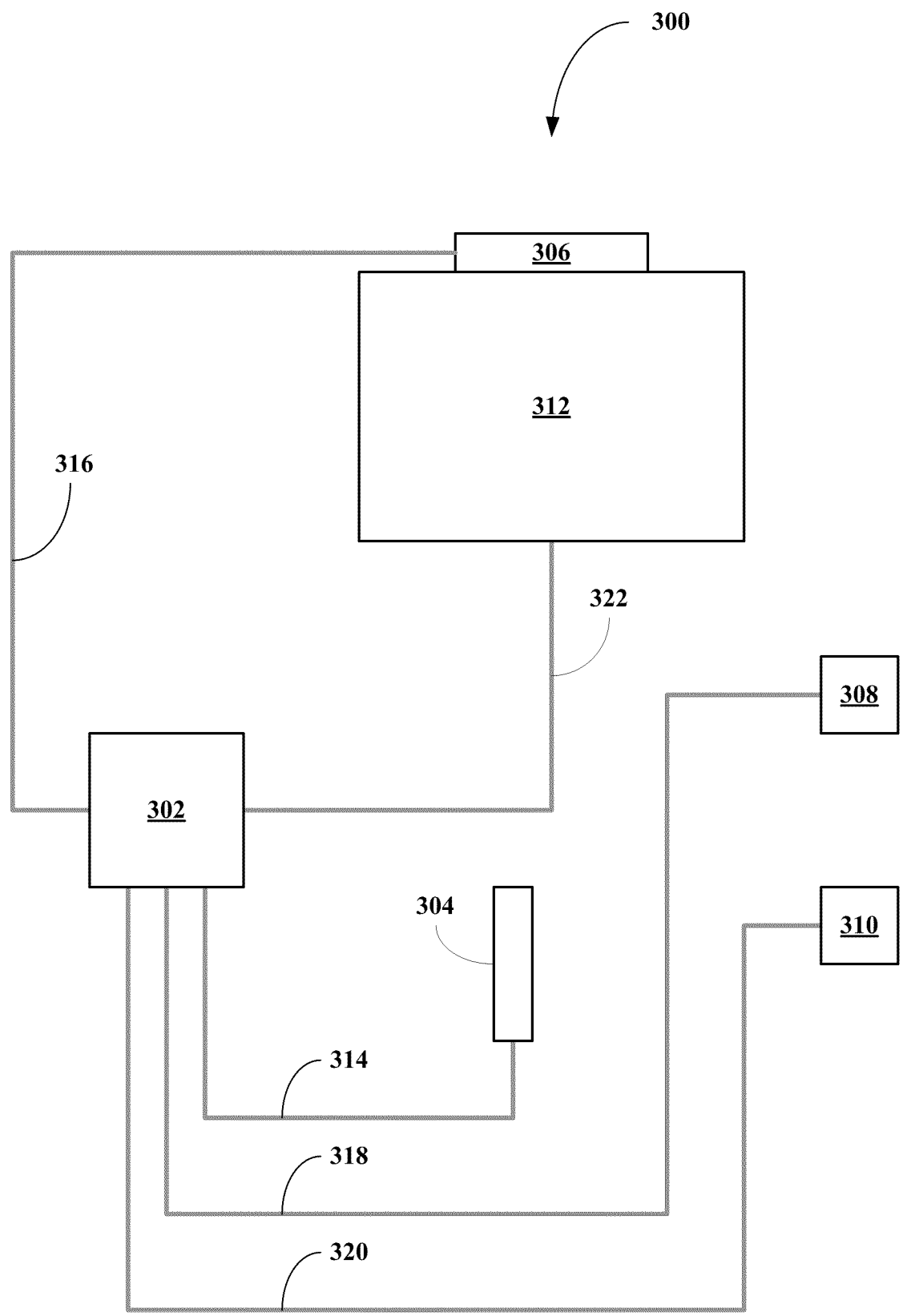
FIG. 3 depicts an embodiment of a system of this invention.

Referring now to FIG. 3, an embodiment of a system of this invention, generally 300, is shown to include a game unit 302. The system 300 also includes a game controller 304, a receiving signal sensor 306, a first transmitting sensor 308, a second transmitting sensor 310 and a display unit 312. The first transmitting sensor 308 is adapted to be associated with a patient's normal limb, while the second transmitting sensor 310 is adapted to be associated a portion of the patient's body adjacent a missing limb. The transmitting sensors 308 and 310 send position data to the receiving sensor 306. When position data is received by the receiving sensor 306, the receiving sensor 306 produces output to the game unit 302, which uses the signals to display a visual representation of the patient's missing limb, or the patient's missing and normal limbs, undergoing an activity in accord with the game currently running on the game unit 302. The displayed activity involving use of the missing limb serves as a feedback to reduce phantom limb pain. The controller 304 is in communication with the game unit 302 via a first communication pathway 314. The receiving sensor 306, the first transmitting sensor 308 and the second transmitting sensor 310 are in communication with the game unit 302 via a second, third and forth communication pathways 316, 318, and 320, respectively. The display unit 312 is in communication with the game unit 302 via a fifth communication pathway 322. All of the pathways may be wired or wireless and may be unidirectional or bidirectional depending on the components and the configuration of the components.

Figure 4:
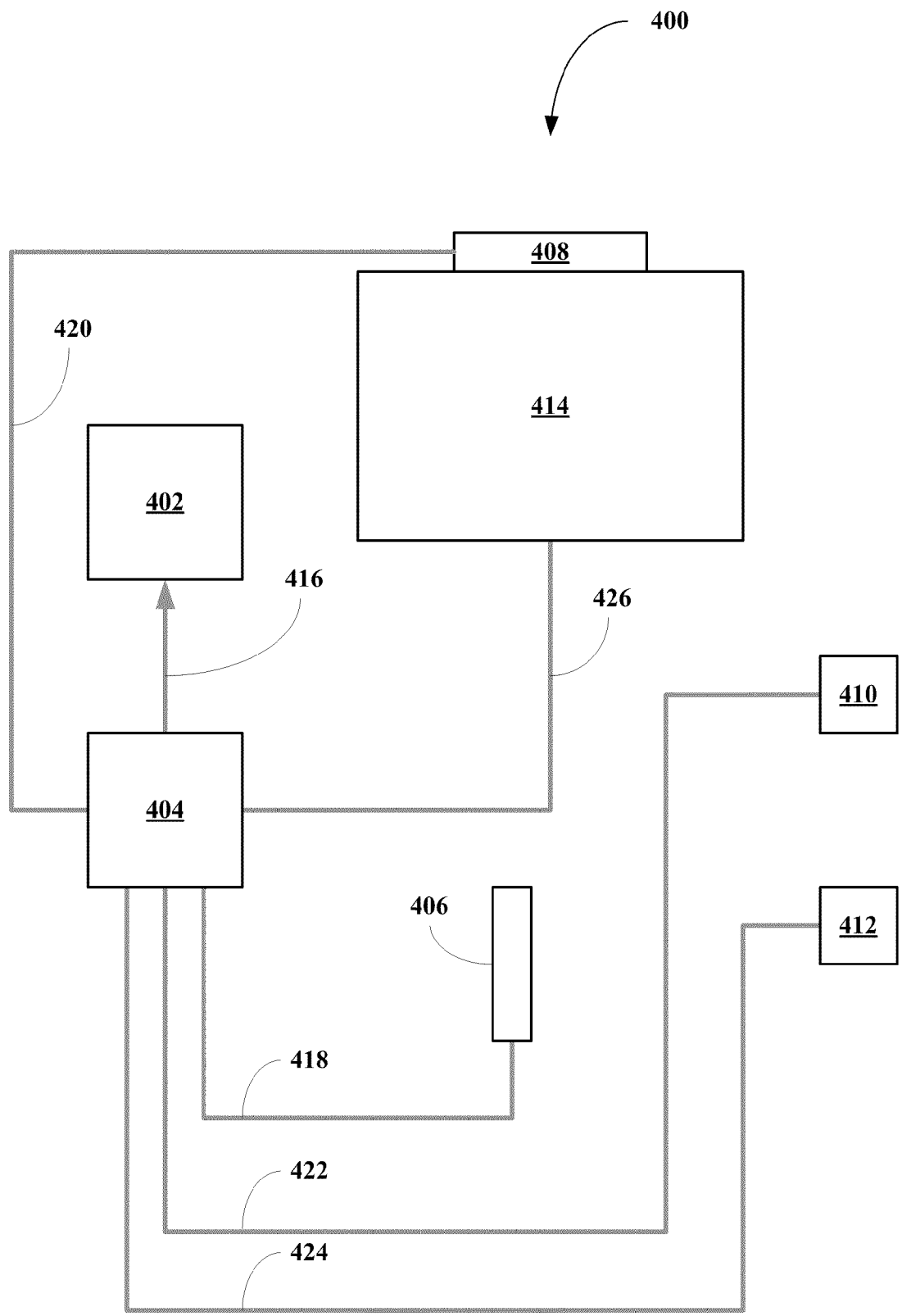
FIG. 4 depicts another embodiment of a system of this invention.

Referring now to FIG. 4, another embodiment of a system of this invention, generally 400, is shown to include a virtual feedback digital processing unit 402 and a game unit 404. The virtual feedback digital processing unit 402 includes an image of a missing limb of a patient, where the image is either generated from a mirror image of a patient's normal limb or is computer generated. The virtual feedback unit 402 supplies the image to the game unit 404, which uses the image to display a patient's missing limb. The system 400 also includes a game controller 406, a receiving signal sensor 408, a first transmitting sensor 410, a second transmitting sensor 412 and a display unit 414. The first transmitting sensor 410 is adapted to be associated with a patient's normal limb, while the second transmitting sensor 412 is adapted to be associated a portion of the patient's body adjacent a missing limb. The transmitting sensors 410 and 412 send position data to the receiving sensor 408 When position data is received by the receiving sensor 408, the receiving sensor 408 produces output to the game unit 404, which uses the signals and the image from the virtual feedback unit 402 to display a visual representation of the patient's missing limb or the patient's missing and normal limbs undergoing an activity in accord with the game currently running on the game unit 404. The displayed activity involving use of the missing limb serves as a feedback to reduce phantom limb pain. The virtual feedback unit 402 is in communication with the game unit 404 via a first communication pathway 416. The controller 406 is in communication with the game unit 404 via a second communication pathway 418. The receiving sensor 408, the first transmitting sensor 410 and the second transmitting sensor 412 are in communication with the game unit 404 via a third, fourth and fifth communication pathways 420, 422, and 424, respectively. The display unit 414 is in communication with the game unit 404 via a sixth communication pathway 426. All of the pathways may be wired or wireless and may be unidirectional or bidirectional depending on the components and the configuration of the components.

Figure 5:
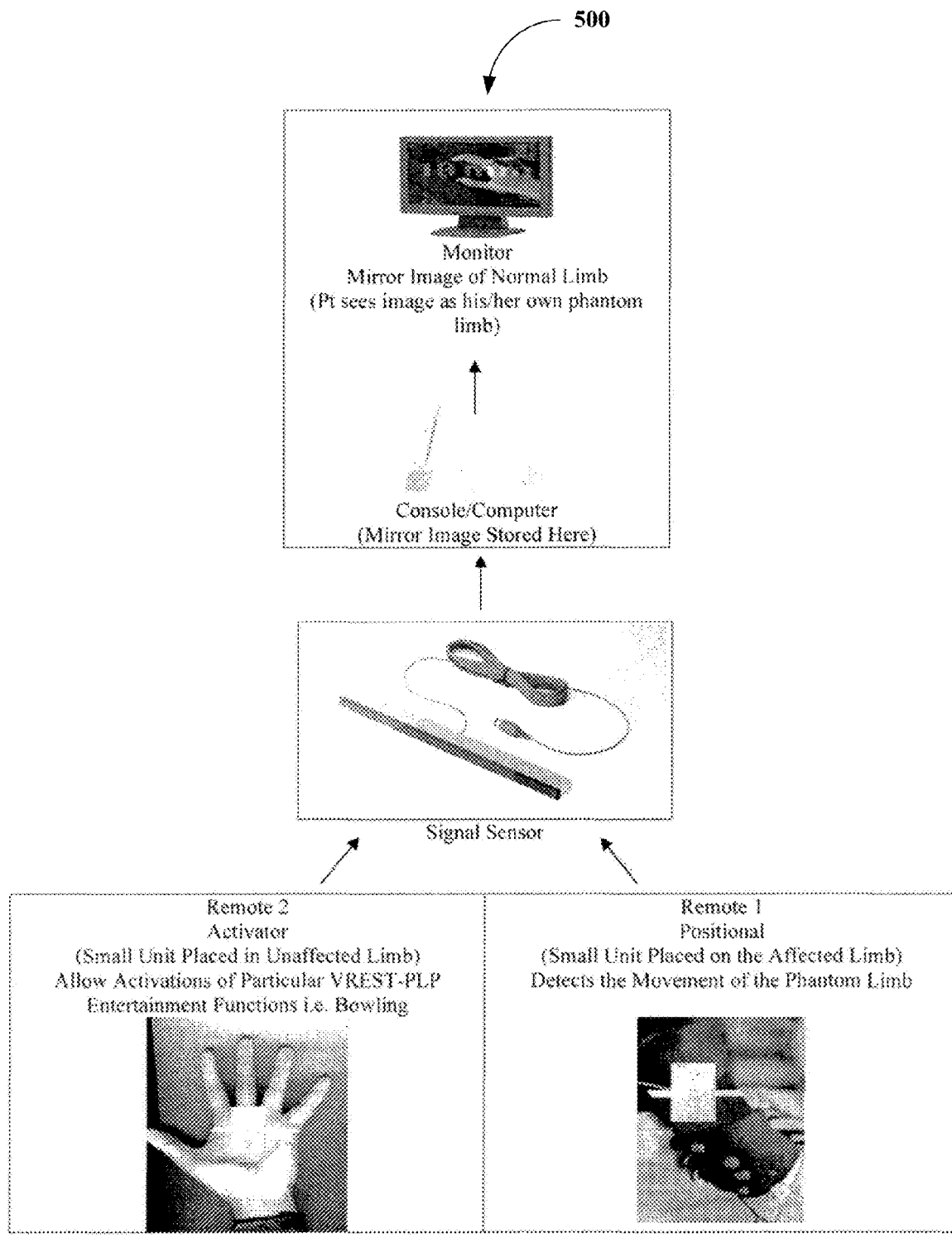
FIG. 5 depicts another embodiment of a system of this invention.

Referring now to FIG. 5, another embodiment of a system of this invention, generally 500, is shown. Remote 1 having a stored image of a phantom or missing limb will be placed on a patient's body near the amputated or missing limb. It will send the position data to a signal sensor. When Remote 1 moves corresponding to motion of the missing limb, the signal sensor receives a signal from Remote 1 corresponding to the movement and patient sees the movement of the missing limb on a television monitor. This provides the visual feedback to the brain of the patient using the missing limb itself reducing PLP in the patient.

A second sensor Remote 2 will be placed on a normal limb. Remote 2 will allow the patient to activate the particular function of the game they are playing, e.g., throwing a bowling ball, while playing bowling. Such interactive games then can be played by the patient displaying the patient having and using the missing limb, thus supplying visual feedback to treat PLP and reduce PLP symptoms. Suppose the patient had the right forearm amputated. Remote 1 can be placed on the elbow of the amputated arm. Remote 2 will be placed in the left or normal hand. When the patient is ready to discharge the bowling bowl, the signal sensor will sense the motion and display a generated image of the right arm, where the generated image may be generated from a mirror image of the left hand that is stored in the computer. Thus, the patient sees the right hand (phantom) in motion on the television screen. The patient will trigger the activity of discharging the bowling bowl with the Remote 2 in the left hand. The television monitor will show the patient throwing a bowling bowl with his right hand. This then will provide the visual feedback from the phantom hand to the brain. Such a device will be interactive, fun, and provide a continuous visual feedback to the brain.

All references cited herein are incorporated by reference. Although the invention has been disclosed with reference to its preferred embodiments, from reading this description those of skill in the art may appreciate changes and modification that may be made which do not depart from the scope and spirit of the invention as described above and claimed hereafter.

We claim:

1. A visual feedback system for treating a patient's phantom limb pain, comprising:
   a game console configured for the patient to play a game, wherein the game is activated by motion of a normal limb of the patient;
   a display in communication with the game console configured to display the played game to the patient;
   a first transmitter affixable to a portion of the patient's body adjacent a missing limb;
   a second transmitter affixable to a normal limb of patient; and
   a receiver in communication with the game console, wherein the receiver receives signals from the first and second transmitters respectively indicative of the motion of the portion of the patient's body adjacent the missing limb and the motion of the normal limb, wherein the motion results from the patient playing the displayed game,
   wherein the game console is configured to output to the display an image of the patient including an image of the missing limb moving as the normal limb moves using the received signals from the first and second transmitters.

2. The system of claim 1, wherein the image of the missing limb is stored in the game console.

3. The system of claim 1, further comprising a digital processing unit, wherein the digital processing unit stores the image of the missing limb and is configured to provide the image to the game console.

4. The system of claim 1, further comprising at least one additional transmitter affixable to other parts of the patient's body, wherein the receiver further receives signals from the at least one additional transmitter indicative of the motion of the other parts of the patient's body, wherein the game console is further configured to output to the display an image of the other parts
   of the patient's body using the received motion from the at least one additional transmitter.

5. The system of claim 1, wherein the image of the missing limb comprises a mirror image of the normal limb.

6. The system of claim 5, further comprising a mirror box, wherein the mirror image of the normal limb is formed by the patient placing their normal limb in a mirror box.

7. A method for providing visual feedback for treating a patient's phantom limb pain, comprising:
   receiving at a receiver signals from a first transmitter affixable to a portion of the patient's body adjacent a missing limb and signals from a second transmitter affixable to a normal limb of the patient, wherein the signals are received in response to movement of the patient while playing a motion-activated video game operating on a game console and displayed on a display;
   providing the received signals from the receiver to a game console, wherein the game console retrieves a stored image of the missing limb; and
   displaying the image of the missing limb on the display, wherein the displayed image simulates the appearance of the missing limb moving as the normal limb moves to perform an action in the video game.

8. The method of claim 7, wherein the image of the missing limb is stored in the game console.

9. The method of claim 7, wherein the image of the missing limb is stored in a digital processing unit associated with the game console.

10. The method of claim 9, wherein the image of the missing limb is formed by producing a mirror image of the normal limb.

11. The method of claim 10, wherein the mirror image of the normal limb is formed by the patient placing their normal limb in a mirror box.

12. The method of claim 7, wherein the image of the missing limb comprises a mirror image of the normal limb.

* * * * *